(12) United States Patent
Hotier

(10) Patent No.: US 6,537,451 B1
(45) Date of Patent: Mar. 25, 2003

(54) ROTARY VALVE

(75) Inventor: Gérard Hotier, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 65 days.

(21) Appl. No.: 09/590,120

(22) Filed: Jun. 9, 2000

(30) Foreign Application Priority Data

Jun. 9, 1999 (FR) .............................................. 99 07308

(51) Int. Cl.[7] .............................................. B01D 15/08
(52) U.S. Cl. .............................. 210/198.2; 137/625.11; 137/625.15; 137/625.46; 210/659
(58) Field of Search ................... 210/635, 656, 210/659, 198.2, 424; 137/625.11, 625.15, 625.46

(56) References Cited

U.S. PATENT DOCUMENTS

| | | | |
|---|---|---|---|
| 3,040,777 A | 6/1962 | Carson | 137/625.15 |
| 3,422,848 A | 1/1969 | Liebman | 137/625.11 |
| 4,614,204 A | 9/1986 | Dolejs | 137/625.46 |
| 4,614,205 A * | 9/1986 | Oroskar | 137/625.11 |
| 4,632,149 A * | 12/1986 | Oroskar | 137/625.11 |
| 4,633,904 A | 1/1987 | Schumann | 137/625.15 |
| 4,705,627 A | 11/1987 | Miwa | 210/264 |
| 4,923,616 A | 5/1990 | Hirata | 210/676 |

* cited by examiner

*Primary Examiner*—Ernest G. Therkorn
(74) *Attorney, Agent, or Firm*—Millen, White, Zelano & Branigan, P.C.

(57) ABSTRACT

Disclosed is a rotary valve that makes it possible to link several groups of hoses referenced group $G_1$, group $G_2$, and group $G_3$. The valve includes a stator (40) that is provided with means (E, F, R, S) for circulating fluid or fluids of group 1, means (45, 46) for passing at least two fluids $F_1$, $F_2$ that belong to group $G_3$, and a rotor (47) that is equipped with means (9) for passing fluids of group $G_3$ and also means (50) that make possible the linking either of fluids of $G_1$ with group $G_3$ or fluids of group $G_3$ with $G_3$.

6 Claims, 4 Drawing Sheets

ROTARY VALVE

The invention relates to a rotary valve that comprises several means that allow the circulation of fluids, whereby the means are arranged to produce the simultaneous linking of different hoses according to a predetermined sequence.

A valve according to the invention is used in particular to link several hoses that can be classified in several groups, defined, for example, according to their function. The connection between the different groups is made, for example, according to a predetermined sequence.

The invention is used, for example, in a process for separation that uses four process fluids such as feedstock, extract, raffinate and desorbent. The different groups can be specified in the following manner:

GROUP 1, $G_1$=the hoses that allow the transfer of fluids from said process fluids, such as extract, raffinate, feedstock and desorbent;

GROUP 2, $G_2$=the hoses that allow the linking to be carried out between the different openings that are arranged at the rotary valve;

GROUP 3, $G_3$=the hoses that allow a process fluid to communicate with a bed of a separation column or between two beds (bypass fluid).

The concept of group that is provided relative to hoses can be extended within the scope of this application to the fluids in question.

By using a single device, the prior art describes the possibility of linking, on the one hand, four external flows (solvent, extract, feedstock, raffinate) and two rinsing flows (inlet and outlet), and, on the other hand, producing 24 connections to 24 adsorbent beds.

For example, U.S. Pat. No. 3,040,777 and U.S. Pat. No. 3,422,848 describe rotary valves that comprise a rotor and a stator.

In U.S. Pat. No. 3,040,777, the rotor comprises on its lower face several grooves for the circulation of process fluids, whereby each groove communicates with a line for admission or evacuation of these fluids. Several openings that are distributed along a circle pass through the stator according to its thickness. These openings communicate with the 24 lines that allow the connection with 24 beds of a separation column. Channels for the passage of two rinsing flows are arranged in the central zone of the stator. A liner that is arranged on the upper face of the stator ensures the sealing between the grooves, between the grooves and the 24 orifices of the 24 beds and also between the 24 orifices. An upper dome in airtight connection with the stator forms a chamber. A fluid that is introduced by a hose in connection with the dome puts the chamber under pressure.

U.S. Pat. No. 3,422,848 relates to an improved liner for withstanding problems of erosion and mechanical deterioration that is produced by the stator-rotor contact, when these two elements are rotating. In this document, the grooves are arranged on the upper face of the stator in a manner that is concentric to the center or axis of rotation of the valve. The communication between the grooves and the orifices for circulation of fluids is ensured by "U"-shaped or jumpover hoses.

In practice, these two types of valves that are widely used have good operating reliability. They are limited, however, in their applications. For example, used in separation processes in a simulated moving bed, they do not make it possible to carry out a continuous rinsing of all of the distribution tentacles and of all of the lines that connect the beds to the rotary valve is not feasible. Inlet and outlet rinsing lines are provided to balance in part this drawback.

The prior art also describes two adaptations of the above-mentioned valves for specific communications of the inlet and the outlet of each of the beds with the four or six inlet or outlet flows.

U.S. Pat. No. 4,614,204 maintains the principle of concentric grooves, while U.S. Pat. No. 4,633,904 describes the use of a number of openings that are used at the stator instead of grooves.

These two latter teachings relate to a rotary valve for the connection of a series of independent columns that each contain an adsorbent bed, with the following particular feature: the end of each of these columns may or may not be connected to the next. The stator comprises two series of orifices that are arranged along two concentric crowns. A first series of orifices is connected to the inlet of each of the columns, and a second series of orifices is connected to the outputs of the columns.

The function of these orifices is to ensure the passage of fluids between the separation columns. Because of the similarity of the circulating fluids, the orifices of the first series have, for example, identical characteristics to the orifices of the second series. The number of hoses for linking, two by two, three groups of openings of the stator (column inlet, column outlet and communication to an outside fluid) is naturally much larger than the six flows that are provided in U.S. Pat. No. 3,422,848. For 24 beds and six outside flows, there are thus 30 linking hoses that have to stand in the small space constituted by the upper stator.

Finally, the prior art can be illustrated by U.S. Pat. No. 4,923,616 and U.S. Pat. No. 4,705,627.

The object of this invention is a rotary valve that makes it possible to link different groups of hoses as defined above.

The rotary valve according to the invention pertains particularly well to a chromatographic separation column of at least one aromatic isomer with 8 carbon atoms in a simulated moving bed in a mixture of xylenes and ethylbenzene by containing, and preferably paraxylene, with a view to the terephthalic acid synthesis, an intermediate petrochemical product in the production of textiles.

More generally, it can be used in a process for separation of at least one isomer in a mixture of components that is difficult or impossible to separate by distillation or by crystallization.

It can also be applied in a process for separation of at least one component in a mixture where an adsorption or ion-exchange chromatographic separation is used, for example.

It pertains in particular to improving the process and the device that are described in Patent Application FR 97/16, 273. In short, this application teaches in particular taking a portion of the main fluid to reinject it into the circulation space of a sector where the pressure is lower via the orifices of the distribution chambers in question.

When the distribution chambers are connected with the outside of the column by a single distribution basket, and when it is desired to establish circulation between two consecutive adsorbent beds, the diagram of individual valves and bypass lines that is provided in the above-mentioned patent application would lead to a parasitic circulation parallel to the separation column.

When each of the distribution plates is equipped with at least two independent fluid distribution networks ($D_1$ and $D_2$), for example, network $D_1$ of plate P is linked with network $D_2$ of plate P+1, and network $D_2$ of plate P+1 is linked with network $D_1$ of plate P+2. In this way, for each of the distributor plates, all of the distribution networks permanently channel a circulation of fluid, and each of the plates experiences a first flow of bypass fluid from a distribution network to the main fluid and a second flow of bypass fluid that is approximately equal from the main fluid to the second distribution network. The driving force of these flows is ensured by the pressure drop that is caused by the flow of main fluid into the porous granular medium that is located between two successive distributor plates.

When each of the distributor plates is equipped with only a single distribution network, the bypass lines can establish only one bed out of two, for example, from plate P to plate P+1, then from plate P+2 to plate P+3. Actually, if a bypass line connected plates P+1 and P+2, a circulation that is parallel to the adsorbent beds from the top bed to the bottom bed would result. To establish the bypass only in one bed out of two would involve a variation of the internal flows from one bed to the next. In the beds that comprise a bypass, a flow rate D would result while on the beds that do not comprise a bypass, a flow rate of D+d would result.

This invention relates to a rotary valve that makes it possible to link several groups of hoses referenced group $G_1$, group $G_2$ and group $G_3$, whereby said valve comprises at least:

- a stator that is provided with means (E, F, R, S) for circulating fluid or fluids of group $G_1$, means for passing at least two fluids $F_1$, $F_2$ that belong to group $G_{31}$,
- a rotor that is equipped with means for passing fluids of group $G_3$ and also means that make possible the linking either of fluids of group $G_1$ with group $G_3$ or fluids of group $G_3$ with group $G_3$.

The valve is characterized in that the number of means for passing for fluid $F_1$ is approximately identical to the number of means for passing for fluid $F_2$, said valve comprises means for linking at least two fluids of group $G_3$ and in that passage section $S_1$ for openings intended for fluid $F_1$ is different from passage section $S_2$ for openings intended for fluid $F_2$.

According to an embodiment, the means for passing for fluid $F_1$ and for fluid $F_2$ have passage surface areas, respectively $S_1$ and $S_2$, and in that the $S_1/S_2$ ratio is approximately equal to 4, and preferably between 2 and 10.

The means for linking fluids of group $G_3$ consist of, for example, slots that are arranged in a layer of material or liner that is deposited on the lower face of the rotor.

A slot has, for example, a depth "pe," and the value of the depth is at least equal to thickness "e" of the liner.

Circulation means (E, R, S, F) can be formed by several grooves that are arranged on the support face of the stator, and the slots are arranged in, for example, the liner.

The number of circulation means (E, R, S, F) is, for example, equal to 4.

The invention also relates to a system for chromatographic separation of a feedstock in a simulated moving bed separation device that comprises a number of beds ($A_1$ to An) of a solid or an adsorbent that are contained in a column, whereby two adsorbent beds are separated by at least one fluid distributor plate (Pi) between each bed, a distributor plate (Pi) comprises at least one distribution chamber (Ci) that is provided with orifices and a space for circulation of a fluid near said orifices of the chamber, said chamber being connected to a transfer line (Li) that extends between the chamber and a point that is located outside of the column, and whereby line (Bi) makes it possible to inject a bypass fluid, means for circulation of the fluid outside of said separation device. The system is characterized in that transfer lines Li, bypass lines Bi and transfer lines of process fluids are connected with at least one rotary valve V that has one of the characteristics that are mentioned above for the rotary valve according to the invention.

The system comprises, for example, a bypass line Le of at least a portion of the fluid before its introduction into the first stage of said separation column, whereby said line Le is connected to the pumparound line and rotary valve V.

According to an embodiment, the system comprises at least one bypass line Le that is connected between rotary valve V and the pumparound line upstream from the recirculation pump.

The separation column comprises, for example, 24 adsorbent beds.

According to an embodiment, the separation column comprises 24 adsorbent beds that are distributed in two separate chambers and connected via hoses and means for circulation of the fluid.

The invention also relates to a process for separation of a feedstock by chromatography.

The process is characterized in that it comprises at least the following stages:

said feedstock that is to be separated is injected into a separation column that comprises a number of beds ($A_1$ to An) of a solid or an adsorbent that are contained in a chromatographic column, whereby two adsorbent beds are separated by at least one fluid distributor plate (Pi) between each bed, a distributor plate (Pi) comprises at least one distribution chamber (Ci) that is provided with orifices, and a space for circulation of a fluid near said orifices of the chamber, and whereby said chamber is connected to a transfer line (Li) that extends between the chamber and a point that is located outside of the column, and a line (Bi) makes it possible to inject a bypass fluid, means for circulation of the fluid outside of said separation device, various fluids are injected or extracted: at least the process fluids, the bypass fluid and the main fluid in various beds $A_i$, according to a predetermined sequence and via a rotary valve V that has the above-mentioned characteristics for the rotary valve according to this invention, whereby said transfer lines Li, bypass lines Bi and process fluid transfer lines are connected with said rotary valve.

According to an implementation, at least a portion of the main fluid is derived before its injection at the top of the separation column to send it directly to rotary valve V.

For example at the last stage of the separation device, the bypass fluid is sent directly from rotary valve V to the pumparound line upstream from the recirculation pump.

The rotary valve according to the invention, or the separation system that comprises the above-mentioned characteristics or the separation process are used, for example, to separate at least one aromatic isomer with eight carbon atoms in a mixture of xylenes and ethylbenzene.

BRIEF DESCRIPTION OF THE DRAWINGS

The invention will be better understood based on the following figures that illustrate, in a simplified and nonlimiting manner, several embodiments of the device and the related process, among which.

DESCRIPTION OF THE PREFERRED EMBODIMENTS

Figure 1:
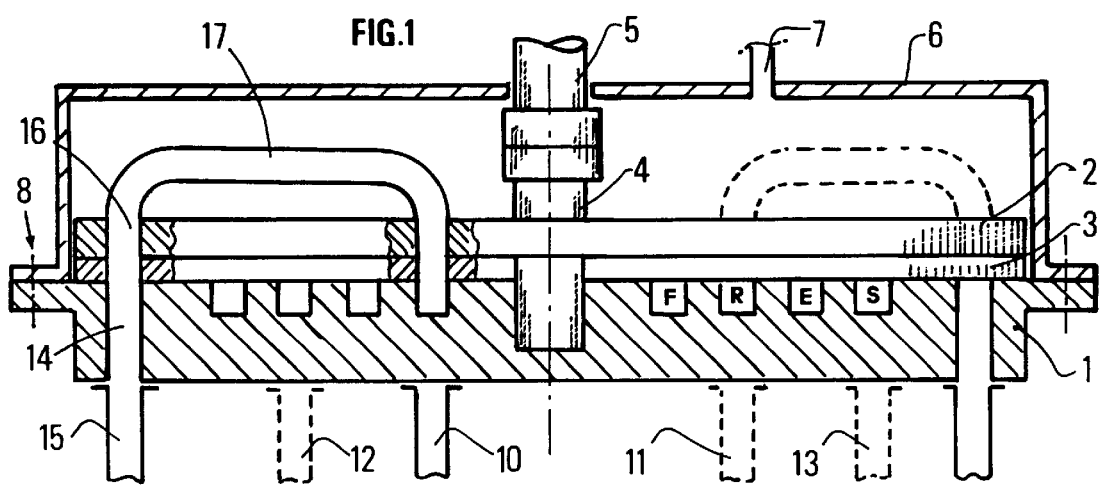
FIGS. 1, 2 and 3 show diagrams of a rotary valve according to the prior art.
Figure 2:
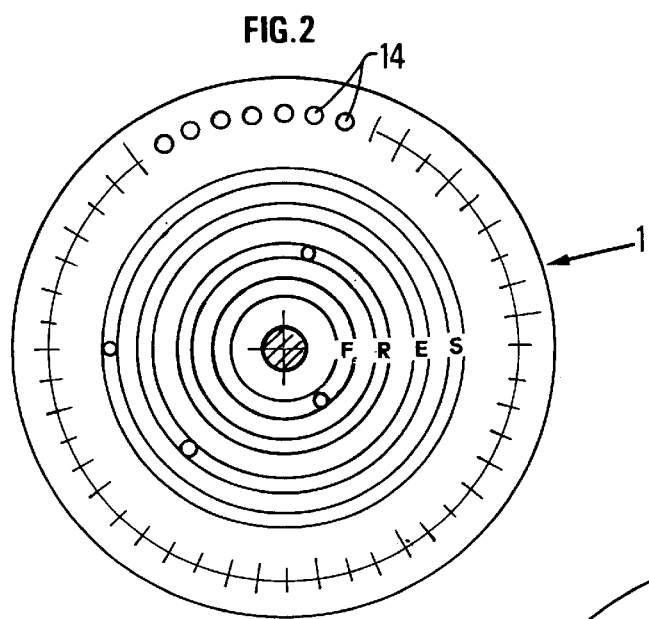
Figure 3:
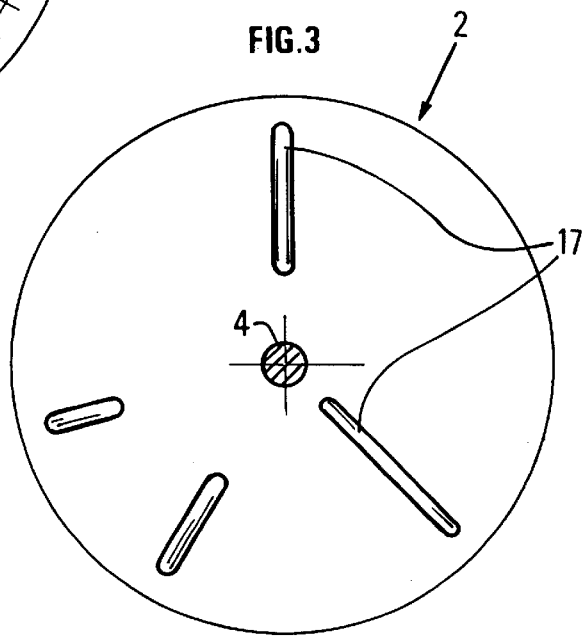

The valve that is described in FIGS. 1, 2 and 3 comprises a lower portion or stator 1 and a rotor 2. A liner 3 or organic material that is arranged, for example, on the lower face of rotor 2 keeps the latter in airtight contact with the stator. The rotor freely rotates via a rotary shaft that comprises two parts 4 and 5 that are coupled to one another, whereby part 5 is accessible from the outside. An upper casing or dome 6 is provided with a hose 7 for introducing a fluid that ensures the pressurization of the unit. This fluid also contributes to ensuring the sealing between the support faces of the stator and the rotor. Dome 6 is in place in the stator with suitable means such as bolts and screws 8.

The upper face of stator 1 comprises several concentric grooves. For example, four grooves F, E, R, S (that correspond respectively in this example to four process fluids: the feedstock, extract, raffinate and desorbent) allow the circulation of the process fluids. Each of them communicate with the outside via at least one hose, respectively 10, 11, 12 and 13. Several openings or hoses 14 that traverse the thickness of the stator are connected to transfer lines 15 toward the outside.

The rotor is provided with openings 16 that traverse it in thickness and that are arranged opposite openings 14 of the stator.

The linking between four grooves F, E, R, S and an opening 14 in question of this stator is carried out with "U"-shaped hoses 17.

Liner 3 consists of a deformable material and ensures the sealing between the grooves, or between the grooves and the openings. It is also selected for facilitating the movements of rotation between the rotor and the stator.

The materials that can be used for the liner can be selected from among the list that is given in, for example, U.S. Pat. No. 3,040,777.

The rotary valve comprises monitoring means and also:
1—Means for indexing, such as a telescopic sight and reference marks intended to ensure the alignment of the means for passing fluid,
2—a brace and gear system to ensure an angular shift by a set angle value based on the predetermined sequence (15°, for example).

The grooves also can be arranged on the lower face of the rotor.

An example of linking between the grooves or the various hoses or openings is provided in, for example, U.S. Pat. No. 3,422,848.

The object of this invention is to design a rotary valve that makes it possible to link several hoses that can be classified according to the different above-mentioned groups $G_1$, $G_2$ and $G_3$.

For example, in the case of an application to a separation process in a column:
$G_1$=the hoses that allow the passage of process fluids (for example, feedstock, extract, raffinate, desorbent),
$G_2$=the hoses that link hoses of group $G_1$ with hoses of group $G_3$ or two different types of hoses of group $G_3$,
$G_3$=it comprises, for example, two series of hoses: the first series ensures the transfer of fluids from the valve to the separation column, and the second series bypasses it (the portion of the main fluid that is sampled and reinjected as a bypass fluid).

Figure 4:
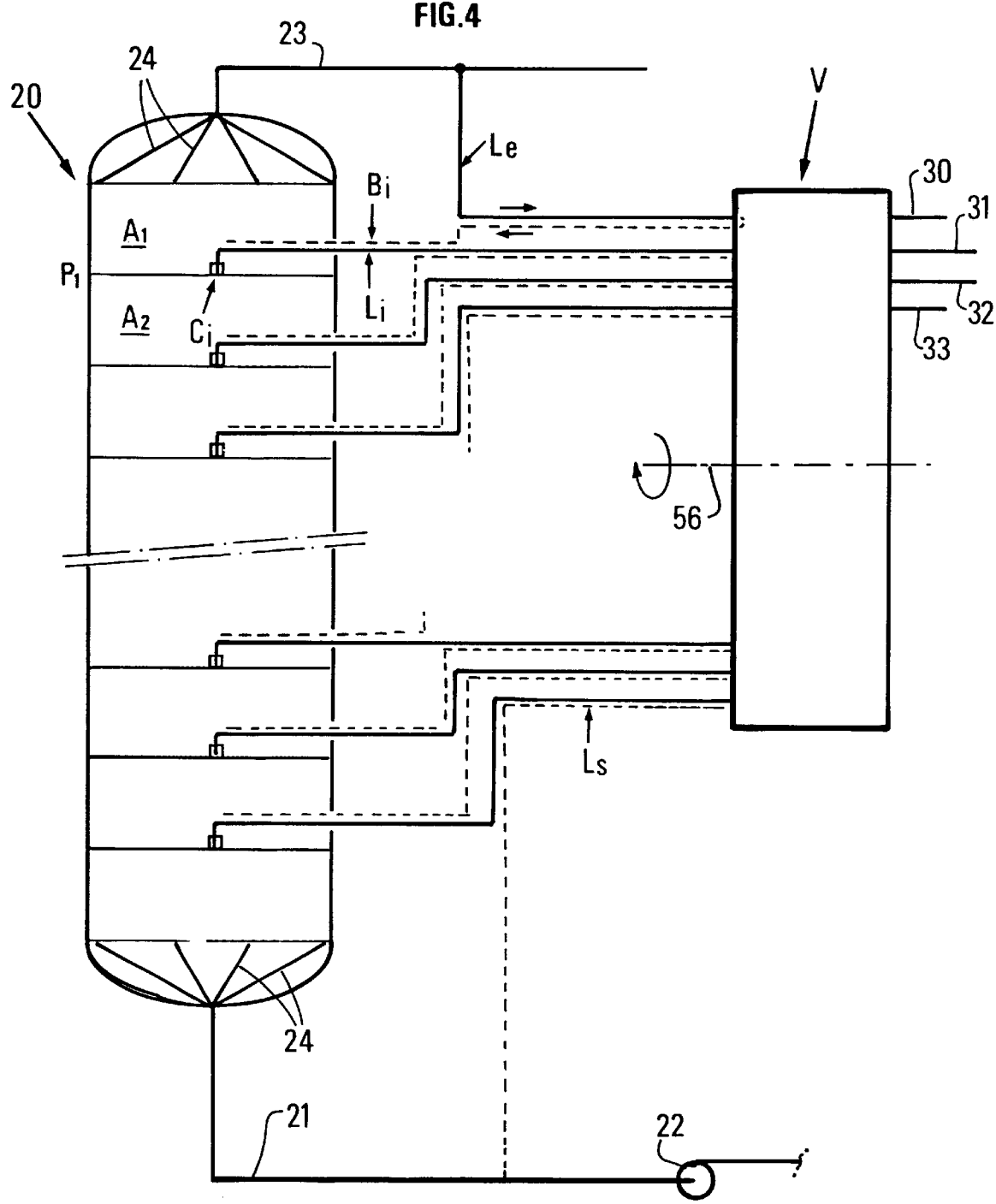
FIG. 4 shows a separation column such as the one that is described in Patent Application FR 97/16,273, to which is attached a rotary valve according to the invention, FIGS. 5, 6 and 7 respectively show a cutaway view of a valve according to the invention, a top view of the stator and a positioning example of the means for linking openings.

The object of this invention is also to design a rotary valve that is used in separation processes where a bypass is produced between each of the beds of a separation column, as it is shown in a diagram in FIG. 4.

FIG. 4 represents a chromatographic column 20 that is cylindrical and that contains a number of beds, An, of an adsorbent such as a zeolitic molecular sieve BaX.

The main fluid is drawn off from the lower end of the column via a pumparound line 21 to be recycled with a pump 22 and a line 23 at the upper end of the column where it is introduced into upper adsorbent bed A, via several lines 24.

For the separation of the paraxylene, starting from a xylene feedstock, for example, generally two columns that comprise twelve beds each are arranged, whereby the 24 beds are divided into at least four zones. One zone is delimited by an injection of a fluid from the outside of the column (or desorbent or feedstock, for example) and a draw-off of another fluid (extract or raffinate, for example). For example, five beds are reserved in zone I, nine beds in zone II, seven beds in zone III, and three beds in zone IV. Distributor plate $P_1$ for fluid that circulates in the following bed is located under bed $A_1$.

A distributor plate $P_1$ is divided into, for example, several plate sectors, according to a cutaway that is described in, for example, Patent Application FR 97/16,273. A sector comprises a fluid distribution chamber $C_i$ that has, for example, a longitudinal shape. A chamber $C_1$ makes it possible to introduce a secondary fluid or to draw off a secondary fluid, and each chamber is connected via a transfer line Li to a rotary valve V that is described in detail in FIGS. 5 to 7.

A line $B_i$ or a bypass line that is connected with rotary valve V and the separation column makes it possible to inject a portion of the main fluid that was sampled at an adsorbent bed $A_i$.

At the top of the column and at the bottom of the column, the arrangement of fluid distribution hoses differs from the one that is adopted at intermediate stages: distributor panels that are located at the inlet of the stage or stages at the top of column 1 or at the outlet of the stage or stages at the bottom of the column(s) do not comprise a distribution basket that is connected to the outside. In these locations, it is not actually necessary to carry out a continuous flushing of fluid. When the column consists of a single part, these inlet and outlet stages correspond to stages that are referenced 1 and 24.

To carry out the bypass function at the top and the bottom of the column:
a line $L_e$ makes it possible to derive, before its introduction at the top of the column, a portion of the fluid that circulates in pumparound line 21 to send it to rotary valve V at an opening 45 of the stator,
a line $L_e$ is connected, on the one hand, to rotary valve V, and, on the other hand, to pumparound line 21, to inject the bypass fluid upstream from fluid recirculation pump 22.

Also shown in FIG. 4 are four hoses 30, 31, 32, 33 that are connected to rotary valve V that are intended for the passing of process fluids such as the feedstock, extract, raffinate and desorbent.

These four hoses are connected with distributor plates $P_1$ using rotary valve V via suitable means that are described in FIGS. 5 to 7 below.

Example for Comparison Between the Stages of a Cycle According to the Prior Art and According to the Invention The following example that is provided by way of illustrative and nonlimiting example relates to the hose between beds $A_1$ and $A_2$ and a separation column that comprises, for example, 24 absorbent beds.

| Position of the Valve | Prior Art | Invention |
|---|---|---|
| 1 | Injection of the feedstock in bed $A_2$ | Injection of the feedstock in bed $A_2$ |
| 2 | Injection of the rinsing fluid in bed $A_2$ | Bypass flow between the plate and the rotary valve |

-continued

| Position of the Valve | Prior Art | Invention |
|---|---|---|
| 3 | None | Bypass flow between the plate and the rotary valve |
| 4 | None | Bypass flow between the plate and the rotary valve |
| 5 | None | Bypass flow between the plate and the rotary valve |
| 6 | None | Bypass flow between the plate and the rotary valve |
| 7 | None | Bypass flow between the plate and the rotary valve |
| 8 | None | Bypass flow between the plate and the rotary valve |
| 9 | None or option (*) | Bypass flow between the plate and the rotary valve |
| 10 | Draw-off of extract from bed $A_1$ | Draw-off of extract from bed $A_1$ |
| 11 | None | Bypass flow between the plate and the rotary valve |
| 12 | None | Bypass flow between the plate and the rotary valve |
| 13 | None | Bypass flow between the plate and the rotary valve |
| 14 | Draw-off of rinsing fluid | Bypass flow between the plate and the rotary valve |
| 15 | Injection of solvent in bed $A_2$ | Injection of solvent in bed $A_2$ |
| 16 | None | Bypass flow between the plate and the rotary valve |
| 17 | None | Bypass flow between the plate and the rotary valve |
| 18 | Draw-off of raffinate from bed $A_1$ | Draw-off of raffinate from bed $A_1$ |
| 19 | None | Bypass flow between the plate and the rotary valve |
| 20 | None | Bypass flow between the plate and the rotary valve |
| 21 | None | Bypass flow between the plate and the rotary valve |
| 22 | None | Bypass flow between the plate and the rotary valve |
| 23 | None | Bypass flow between the plate and the rotary valve |
| 24 | None | Bypass flow between the plate and the rotary valve |

(*) At stage 9, a possible option consists in injecting the secondary rinsing fluid into bed $A_2$.

In practice, the separation column can consist of two columns that each comprise twelve adsorbent beds that correspond to stages 1 to 12 and 13 to 24. The lower end of the first column is connected with the top of the second column, and the lower end of this second column is connected to the top of the first column with hoses and suitable pumping means that are known to one skilled in the art. In this case, the panels of the inlets that correspond to stages 1 and 13 and of the outlets that correspond to stages 12 and 24 are not flushed by the bypass fluid in a manner that is identical to stages 1 and 24 of a single column.

Figure 5:
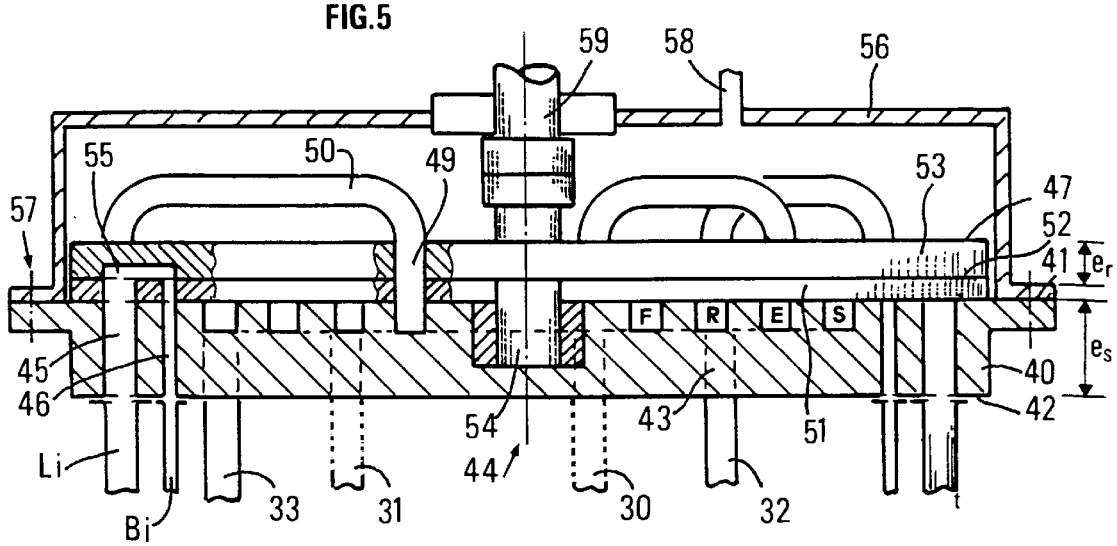
Figure 6:
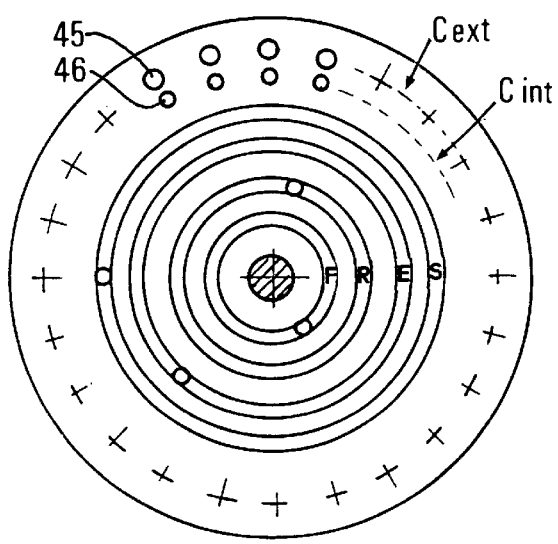
Figure 7:
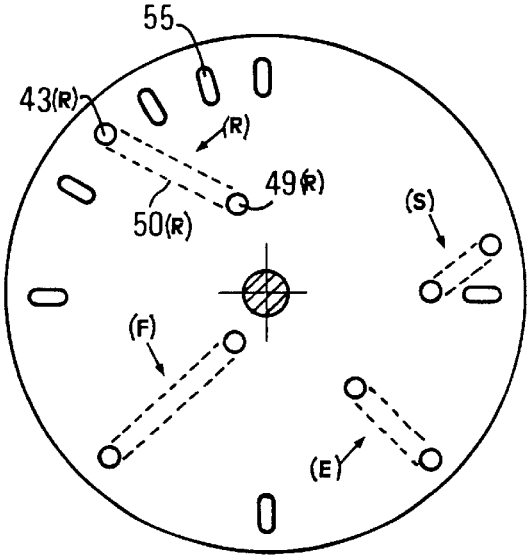
Figure 8:
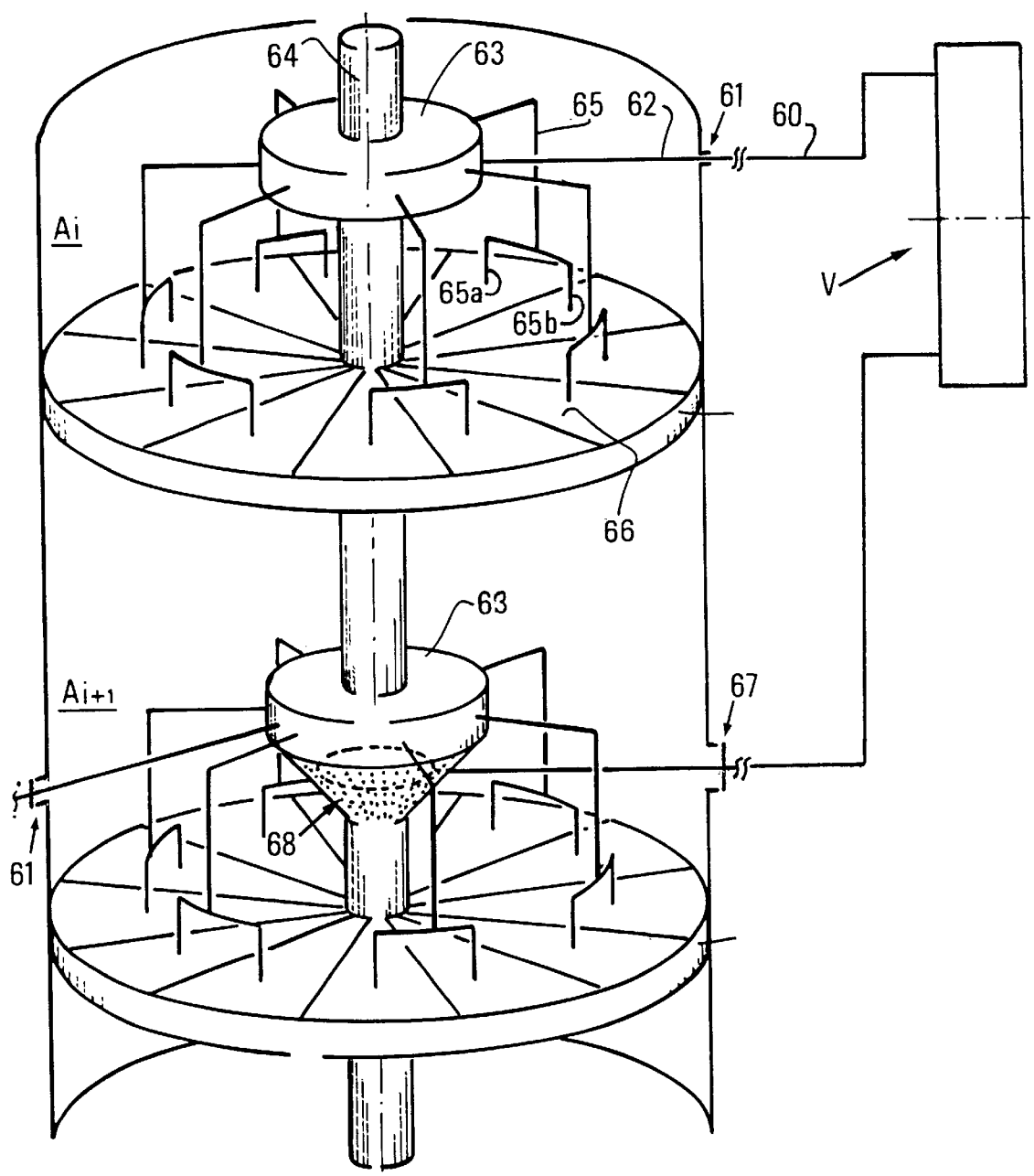
FIG. 8 shows a diagram of an example of connecting the valve according to the invention with a separation unit.

FIGS. 5, 6 and 7 make it possible to illustrate the valve according to the invention as well as an example for arrangement of the communication means for carrying out a stage of the process.

FIGS. 5 and 6 correspond to a cutaway view of the valve and a top view of the stator.

The rotary valve comprises:
A stator 40 that comprises:
A part of thickness "ee" delimited by an upper face 41 (support face) and a lower face 42.

Starting from the center of the stator, four approximately concentric grooves F, R, E, S are arranged on upper face 41. Each of these grooves is intended for the passage of a process fluid, whereby the distribution can be done according to an order of F, R, E, S or any other order. Each of the grooves is connected with a hose 43 that traverses the thickness of the stator and allows the passage of, for example, process fluids that are obtained from hoses 30, 31, 32, 33.

In the description, grooves F, R, E, and S are part of predefined group $G_1$.

Different possibilities exist for circulating the fluids in the grooves. In FIGS. 5 and 6, the example shows a distribution of the fluids that ranges from more polluting to less polluting from center 44 to the periphery of the stator.

Several openings:
Openings 45 that are each connected to a transfer line Li and with a passage surface $S_1$ are distributed, for example, on a circle $C_{ext}$ (FIG. 6) that is arranged toward the periphery of the stator. The number of these openings 45 is equal to the number of transfer hoses Li,
openings 46 that are each connected with a bypass line (Bi) and with a passage section $S_2$, are arranged on a circle $C_{int}$ (FIG. 6) that is located between the circle that is outermost with respect to the stator and the first groove of the group (in this example groove F).
An opening 46 corresponds to an opening 45.

Passage sections $S_1$ and $S_2$ of openings 45 and 46 are determined based on the flow rate of secondary fluids (or process fluids) and the flow rate of the bypass fluid; whereby the pressure drop is imposed by the granular medium for a given flow rate, and the diameter of the bypass line is selected to comply with synchronism of the flow rates of the main fluid and the bypass fluid. Typically, the value of the $S_1/S_2$ ratio is on the order of 4 and can be between 2 and 10.

A rotor 47 that comprises:
An element with thickness "$e_r$" delimited by a lower face 52 and an upper face 53. The element is mounted on a rotary shaft that comprises two parts 54 and 59 that are coupled to one another.
Part 54 is held in the stator by bearings. Part 59 traverses a bell 56 that is described in detail below, whereby the sealing is ensured by systems that are known to one skilled in the art.
Several openings 49 that traverse the rotor over its thickness. These openings 49 are arranged to link a groove (R, F, S, E) with a process fluid transfer line (30, 31, 32, 33),
means 50 such that the "U"-shaped hoses for linking an opening 49 with an opening 45 of the stator. In this case of application, hoses 50 are four in number,
a seal or liner 51, with thickness e, arranged on lower face 52 of the rotor, ensures the sealing between the four grooves, and various openings 45, 56, 43, means 55 for linking a transfer line Li with a bypass line Bi distributed on upper face 53. These means can consist of elliptical slots, for example, whose large axes are oriented, for example, radially to the rotor.

Slots 55 that are arranged in, for example, the liner have the following characteristics:
  a depth "$p_e$,"
  a main axis that has a sufficient length to link two openings 45 and 46 that are located on the same radius of the stator to produce the bypass. The length of this axis is at least equal to distance "d" that separates two circles $C_{int}$ and $C_{ext}$.

The value of depth "$P_e$" is, for example, greater than the value of thickness "e" of liner 51, whereby at least a portion of slot 55 is made in the liner that is arranged on lower face 52 of the rotor.

A bell 56:

Bell 56 is kept in the stator with means 57 that are known to one skilled in the art, such that screws, bolts or any other means make it possible to ensure a mechanical connection. A line 58 makes it possible to introduce a pressurized fluid. Prior to the rotation of the rotor, the pressure in the bell is lowered to reduce the force that is being exerted between the rotor and the stator and to facilitate the relative displacement between these two parts.

FIG. 6 shows the upper face of the stator, in particular the following elements: openings 45 and 46 that are distributed along two circles, respectively $C_{ext}$ and $C_{int}$, grooves F, R, E and S, and openings 43 that empty into the grooves.

FIG. 7 makes it possible to illustrate an example of linking various elements of the valve during a stage of the process. On the lower face of the rotor, the position of the slots and means 50 were shown when four beds experience the passing of four process fluids, whereas the twenty other beds channel the bypass fluid.

Slots 55 make it possible to let the bypass fluid pass between two consecutive beds, for example.

The four "U"-shaped hoses 50 link an opening of a groove with an outside hose that allows the introduction or the extraction of a process fluid.

Thus, in FIG. 7,
  the raffinate is extracted from bed 4 by passing through an opening 49 (R), a hose 50 (R), an opening 43 (R) and hose 30,
  the feedstock is injected into bed 10 via hose 31, an opening 43 (F), a hose 50 (F), an opening 49 (F),
  the extract is drawn off from bed 16 by passing through an opening 49 (E), a hose 50 (E), an opening 43 (E) and hose 33,
  the solvent or desorbent is introduced into bed 20 via hose 32, an opening 43 (S), a hose 50 (S), an opening 49 (S).

Indices R, F, S and E respectively designate the raffinate, the feedstock, the desorbent and the extract.

The other beds receive the bypass fluid, which corresponds to linking an opening 45 with an opening 46 via a slot 55.

Without exceeding the scope of the invention, it is also possible to produce an elliptical slot in the liner at locations where the secondary fluids are injected or drawn off without exceeding the scope of the invention. In this case, the fluids are injected and drawn-off in part via the bypass line, but the four beds that follow the injections or the draw-offs do not undergo internal flow disturbance due to the interruption of the bypass flow.

The openings of the rotor or the stator can take various shapes, for example egg-shaped, circular, square or rectangular.

The data relative to the feedstock that is to be treated in the sieve and in the desorbent are identical for the two examples:

The feedstock that is to be treated consists of 0.5% of non-aromatic compounds (paraffins and naphthenes), 4.8% of ethylbenzene, 24% of paraxylene, 47.2% of metaxylene, 23.25% of orthoxylene and 0.25% of aromatic compounds with 9 carbon atoms.

The desorbent consists of 98% of paradiethylbenzene and 2% of other aromatic compounds with ten carbon atoms, among which the metadiethylbenzene is in the majority for the most part; water is also injected into the desorbent so that the water content of this mixture is about 180 ppm.

The solid adsorbent is the X zeolite that is loaded with barium, with a grain size of between 0.3 and 1 mm. The operating temperature is 175° C., and the lowest pressure is 0.85 MPa absolute.

A total of 630 m$^3$ of adsorbent is arranged in two columns that are each divided into twelve beds.

Example 1=Use of the Rotary Valve According to the Prior Art (FIGS. 1, 2, 3 and 8)

The rotary valve according to the prior art comprises seven grooves that are concentric to the upper portion of the stator. Twenty-four lines 60 with an inside diameter of 15 cm and a length of 8 m connect rotary valve V to intake flange 61 of each of the 24 beds. Inside each of the intermediate beds, there is a pipe 62 that has an inside diameter of 15 cm and that connects outside flange 61 to a central distributor 63 that is arranged around a non-perforated central mat 64 that is 60 cm in diameter. This part has an inside width of 5 cm and a height of 20 cm. Twelve lines 65 that have a length of 1.80 m and an inside diameter of 6.3 cm connect central distributor 63 to 24 radial distributor panels 66, whereby the lines are distributed every 30°. The end of each of these lines 65 is divided into two lines 65a, 65b that have an inside diameter of 5 cm and a length of 0.8 m, thus making possible the connection to intake flanges of the distribution box of two adjacent distributor panels. The total volume of the lines for connection to the central distributor, the central distributor, the inside line to the outside flange, and the line of the outside flange to the rotary valve is approximately 305 liters.

The external flow rates that move toward or outside of the unit are as follows:
  desorbent 346 m$^3$/h,
  rinsing, outlet 27 m$^3$/h,
  extract 181 m$^3$/h,
  secondary rinsing (that consists of desorbent) 27 m$^3$/h,
  rinsing, inlet (recycling of outlet rinsing) 27 m$^3$/h,
  feedstock 257 m$^3$/h,
  raffinate 449 m$^3$/h.

The internal flow rates of the unit are:
  zone 1A, 1 bed (between the desorbent and the outlet rinsing) 1103 m$^3$/h,
  zone 1B, 3 beds (between the outlet rinsing and the extract) 1076 m$^3$/h,
  zone 2A, 1 bed (between the extract and the secondary rinsing) 895 m$^3$/h,
  zone 2B, 7 beds (between the secondary rinsing and the inlet rinsing) 922 m$^3$/h,
  zone 2C, 1 bed (between the inlet rinsing and the feedstock) 949 m$^3$/h,
  zone 3, 7 beds (between the feedstock and the raffinate) 1206 m$^3$/h,
  zone 4, 4 beds (between the raffinate and the desorbent) 757 m$^3$/h.

For a swapping-out period of the rotary valve of 69 seconds, the measured purity of the paraxylene is 99.74% and the yield is 98.1%.

Example 2=Separation Unit that is Equipped with a Rotary Valve According to the Invention (FIGS. 4 to 8)

The valve does not comprise more than four concentric circular grooves on the upper face of the stator. The 24 lines with an inside diameter of 15 cm, as well as the distribution tentacles, were left in place, in contrast 24 lines with an inside diameter of 8.7 cm were added between the rotary valve and each of the beds according to FIG. 4.

Inspection ports 67 that are present in each adsorbent bed were modified to be equipped with a through flange. The length of each of these bypass lines is also 8 m. A strainer 58 whose upper part rests on the bottom of existing central distributor 63 and whose lower part rests on the non-perforated central tube was installed at each stage; on each bed also a line with a length of 2.4 m and a diameter of 8.7 cm was installed between the strainer and the flange that traverses the inspection port. The volume between the rotary valve and the inlet point in the strainer is about 46 liters for each stage.

The flow that circulates in the bypass line is to be synchronous with the flow that circulates in the bed: two drops of liquid of the same composition, whereby one circulates inside the bed and the other through the bypass line should be found again at the strainer at the same time; i.e., after having traveled through 90% of the volume of the distributor panel unit plus bed for the fluid that remains in the column. In this particular case, the flow that circulates in the bypass lines should be 21.3 m$^3$/h on average.

The pressure drop per bed is 0.035 MPa. In fact, the pressure drop through each of the beds depends on flow rate D in the bed in question by an Ergun-type law known to one skilled in the art.

(Delta $P=k_1*D+k_2*D**_2$, where $k_1$ is considerably larger than $k_2$). This leads to the device being self-regulating: when the internal flow rate increases, the pressure drop also increases, and the bypass flow rate increases. Each bypass line is equipped with a Prandtl-tube-type flowmeter and a butterfly-type control valve to be able to adjust manually each of the flow rates at the time of start-up of the unit (to ensure that all of the bypass lines deliver an essentially identical flow rate for a given inside flow rate). The selection of this flowmeter and this valve is dictated by their reasonable cost and mainly by the fact that they produce only a very small pressure drop in the bypass circuits.

The target flow rates that are sent to the recycling pump are 1145 m$^3$/h in zone 1 (5 beds), 964 m$^3$/h in zone 2 (9 beds), 1221 m$^3$/h in zone 3 (7 beds), and 772 m$^3$/h in zone 4 (3 beds). The internal flow rates of the beds are about 21.3 m$^3$/h lower. The flow rates of extract, feedstock and raffinate have been kept identical, the total desorbent flow rate is also kept identical at 373 m$^3$/h, but the rinsing steps were totally eliminated: the secondary rinsing was thus added to the desorbent. The purity and the yield that are obtained are now respectively 99.81% and 98.75%.

The valve that has one of the characteristics explained in FIGS. 5 to 7 has in particular the advantage of comprising fewer grooves and using less jumpover. It also provides the possibility of producing bypass flows over all of the beds of a separation column that comprises a distribution basket by preventing parasitic circulations.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.308 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

Cross Reference To Related Application

This application is related to applicants concurrently filed application Attorney Docket No. Pet-1855, entitled "MAT ELEMENT THAT HAS A DISTRIBUTION FUNCTION, based on French Application 99/07.307 filed Jun. 9, 1999.

What is claimed is:

1. A rotary valve for linking several groups of hoses referenced group G1, group G2 and group G3, whereby said valve comprises:

a stator comprising:
  a support face,
  at least two concentric grooves arranged on the support face, each groove communicates with one of the hoses of the group $G_1$,
  a first series of at least two passages arranged on a circle Cext concentric of said grooves, each passage of the first series communicates with one hose of the group $G_3$ for passing a fluid $F_1$, and
  a second series of at least two passages arranged on a circle Cint concentric of said grooves, each passage of the second series communicates with one hose of the group $G_3$ passing a fluid $F_2$,
said passages of the first series and said passages of the second series have passage sections respectively $S_1$ and $S_2$, the $S_1/S_2$ ratio is 2 to 10,
a rotor comprising:
  a lower face which is in contact with the support face of the stator, or optionally in contact with the stator through a liner,
  at least two hoses of the group $G_2$ for linking one of said grooves with one of said
  passages of the first series,
  at least two slots arranged on the lower face, or optionally arranged on the liner, for linking one of said passages of the first series with one of said passages of the second series.

2. A rotary valve according to claim 1, wherein the $S_1/S_2$ ratio is 4.

3. A rotary valve according to claim 1, wherein the lower face of the rotor is in contact with the support face of the stator through a liner.

4. A rotary valve according to claim 1, wherein the slots are arranged on the liner.

5. A rotary valve according to claim 1, wherein said slots have a depth which is at least the thickness of the liner.

6. A rotary valve according to claim 1, comprising four grooves.

* * * * *

UNITED STATES PATENT AND TRADEMARK OFFICE
CERTIFICATE OF CORRECTION

PATENT NO. : 6,537,451 B1
DATED : March 25, 2003
INVENTOR(S) : Gerard Hotier

It is certified that error appears in the above-identified patent and that said Letters Patent is hereby corrected as shown below:

Column 12,
Line 61, reads "claim 1" should read -- claim 4 --

Signed and Sealed this

Eleventh Day of January, 2005

JON W. DUDAS
*Director of the United States Patent and Trademark Office*